(12) United States Patent
Brown

(10) Patent No.: US 7,862,529 B2
(45) Date of Patent: Jan. 4, 2011

(54) NEUROMUSCULOSKELETAL KNEE SUPPORT DEVICE

(75) Inventor: Timothy W. Brown, Laguna Beach, CA (US)

(73) Assignee: Intelliskin, LLC, Beverly Hills, CA (US)

(*) Notice: Subject to any disclaimer, the term of this patent is extended or adjusted under 35 U.S.C. 154(b) by 930 days.

(21) Appl. No.: 11/075,038

(22) Filed: Mar. 7, 2005

(65) Prior Publication Data

US 2005/0240134 A1 Oct. 27, 2005

Related U.S. Application Data

(60) Provisional application No. 60/551,167, filed on Mar. 8, 2004.

(51) Int. Cl.
A61F 5/00 (2006.01)
A61F 13/06 (2006.01)
A61F 5/37 (2006.01)

(52) U.S. Cl. .................... 602/26; 602/61; 128/882

(58) Field of Classification Search ............. 602/26, 602/61–63, 27; 128/882, 112.1, 113.1, 114.1, 128/121.1

See application file for complete search history.

(56) References Cited

U.S. PATENT DOCUMENTS

| 3,786,804 A | | 1/1974 | Lewis | |
|---|---|---|---|---|
| 4,008,350 A | * | 2/1977 | Crawford et al. | 521/54 |
| 4,116,236 A | * | 9/1978 | Albert | 602/26 |
| 4,287,885 A | * | 9/1981 | Applegate | 602/26 |
| 4,366,813 A | * | 1/1983 | Nelson | 602/26 |
| 4,445,505 A | * | 5/1984 | Labour et al. | 602/26 |
| 4,561,123 A | | 12/1985 | Hull | |
| 4,986,263 A | | 1/1991 | Dickerson et al. | |
| 5,695,452 A | * | 12/1997 | Grim et al. | 602/6 |
| 5,823,981 A | * | 10/1998 | Grim et al. | 602/26 |
| 5,865,776 A | * | 2/1999 | Springs | 602/26 |
| 6,279,160 B1 | * | 8/2001 | Chen | 2/24 |
| 6,793,641 B2 | * | 9/2004 | Freeman et al. | 602/26 |
| 2004/0153017 A1 | * | 8/2004 | Simmons et al. | 602/26 |
| 2005/0020951 A1 | * | 1/2005 | Gaylord et al. | 602/26 |

OTHER PUBLICATIONS

Definition of Intermediate from dictionary.com.*

* cited by examiner

*Primary Examiner*—Patricia M Bianco
*Assistant Examiner*—Tarla R Patel
(74) *Attorney, Agent, or Firm*—Morgan, Lewis & Bockius LLP

(57) ABSTRACT

A knee brace for proprioceptively treating a patient comprises a sleeve having an anchor strap and a viscoelastic pad. The sleeve defines inner and outer sleeve surfaces and is configured to envelop the patient's knee. The anchor strap is circumferentially wrappable about the outer sleeve surface and defines an inner strap surface. The anchor strap has an intermediate anchor portion disposed on the inner strap surface between opposing end anchor portions that are releasably securable to the outer sleeve surface such that tension in the anchor strap may be selectively adjusted. The knee brace includes an elastic band extending along the inner strap surface. The viscoelastic pad is securable on the inner sleeve surface generally opposite to the elastic band such that pressure may be applied to the patient's infrapatellar tendon when the anchor strap is extended over the outer sleeve surface.

19 Claims, 6 Drawing Sheets

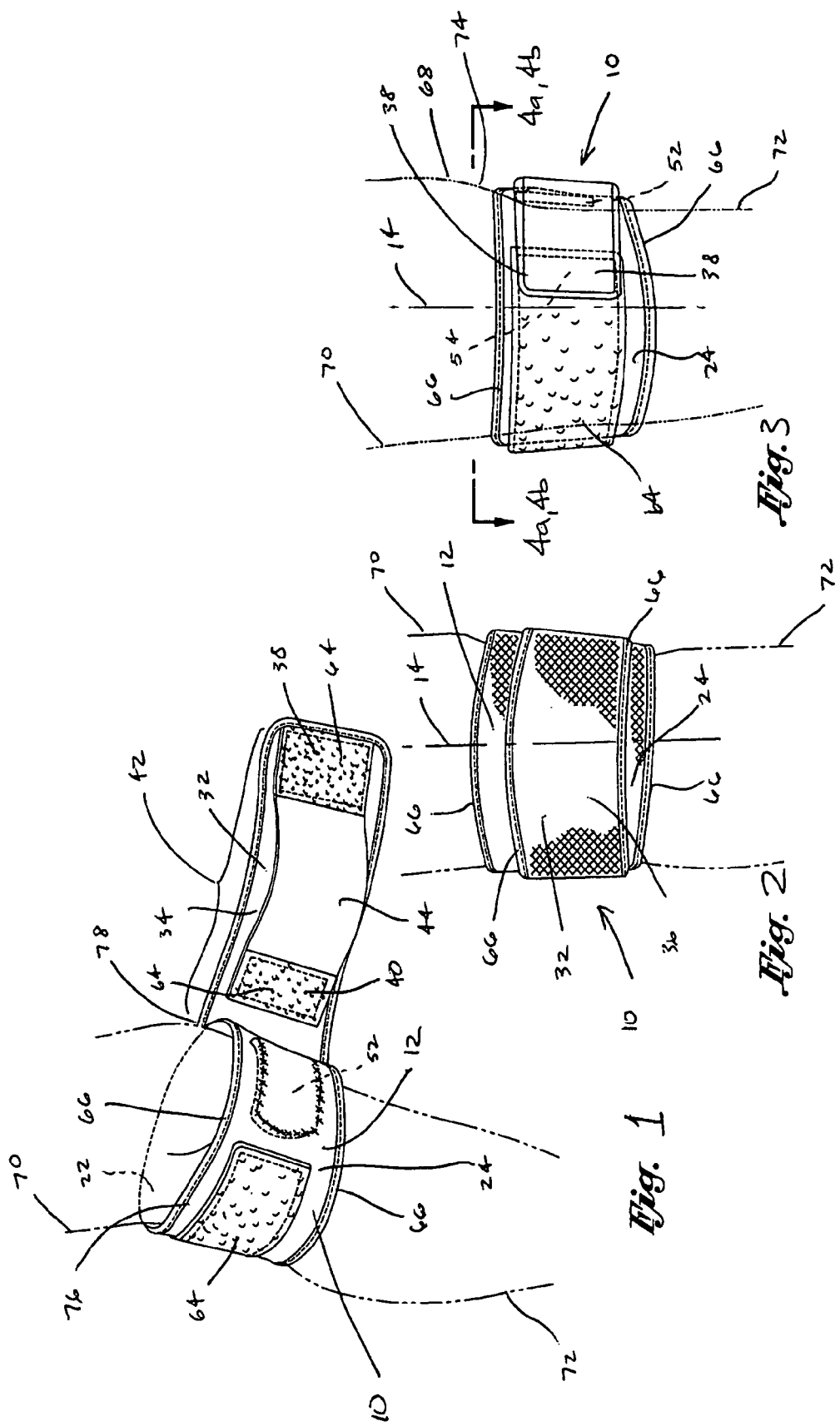

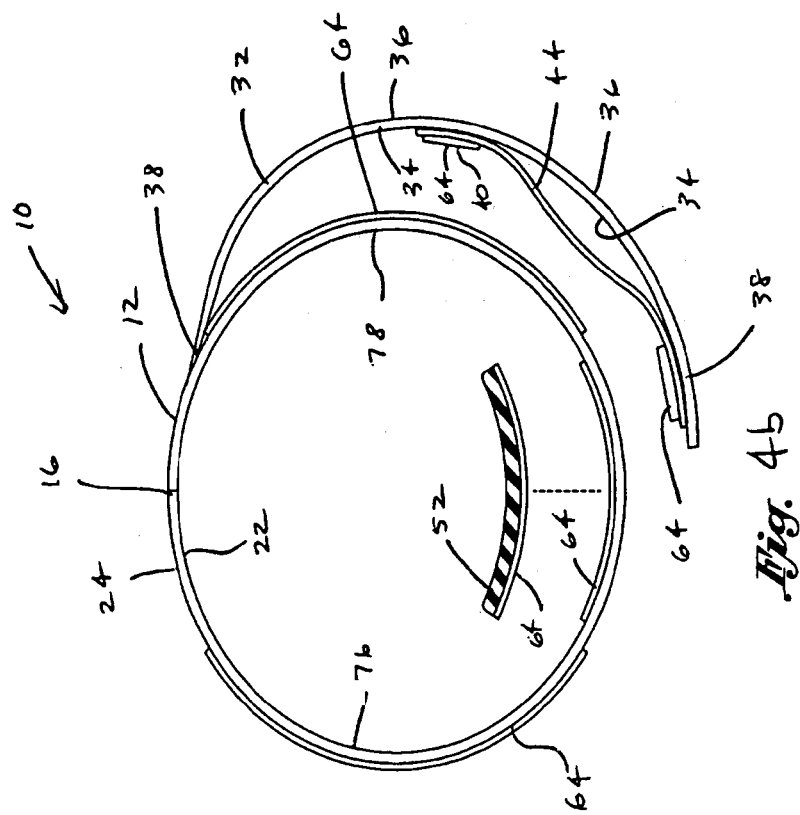
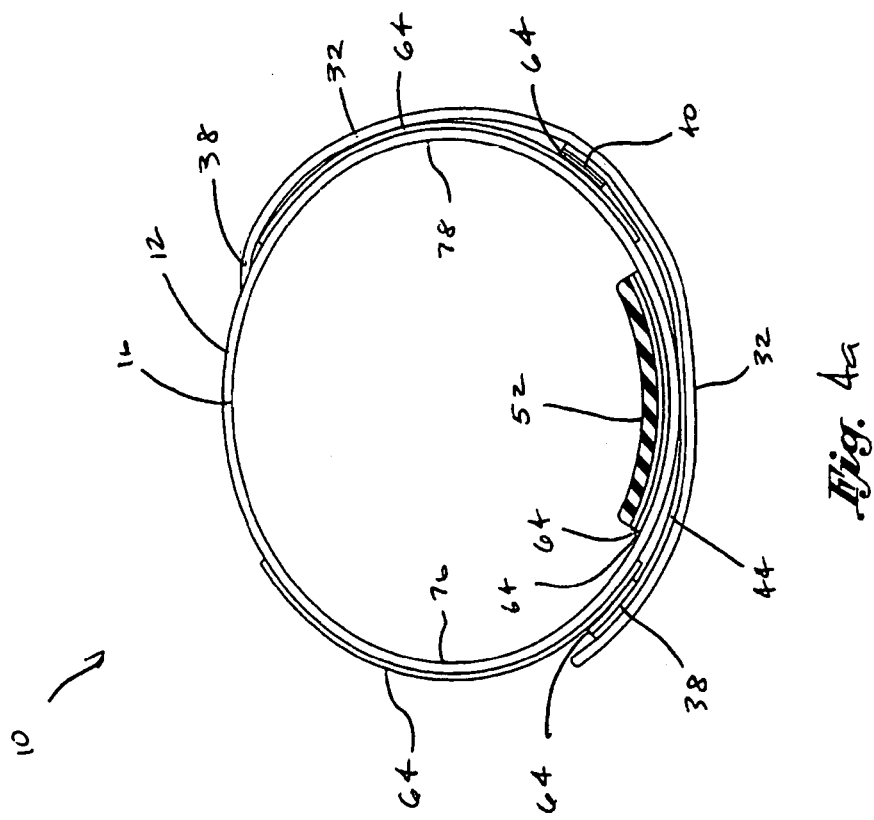

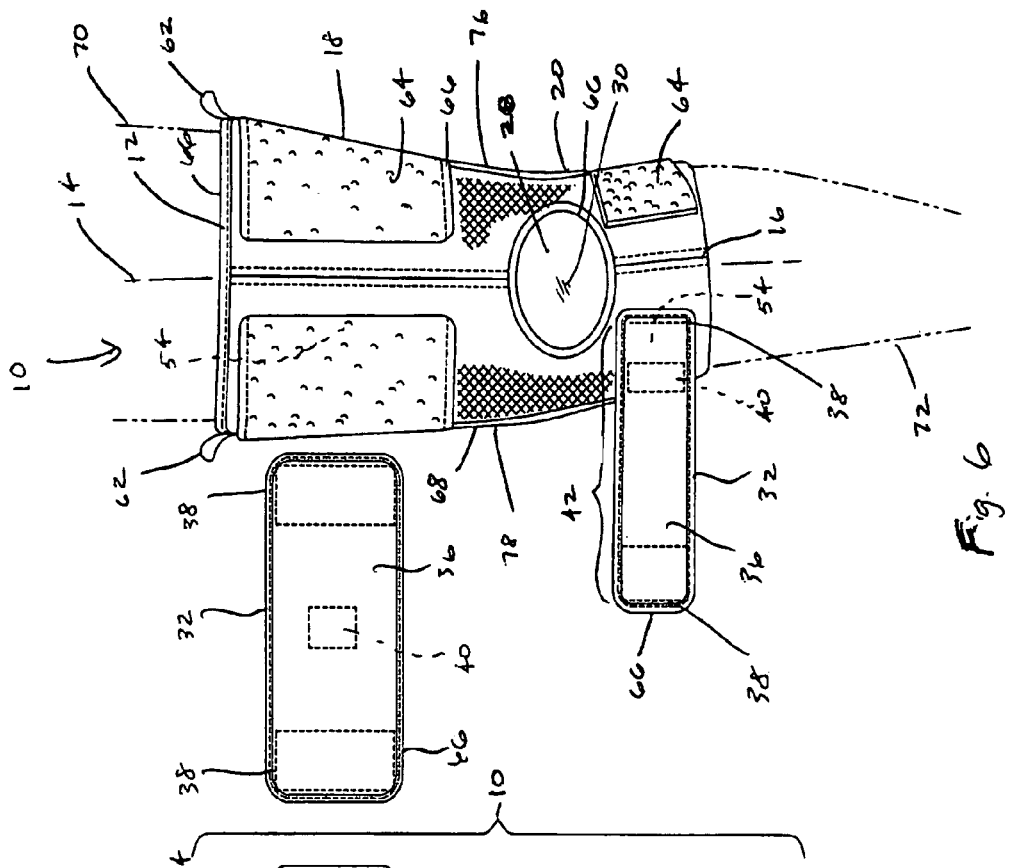

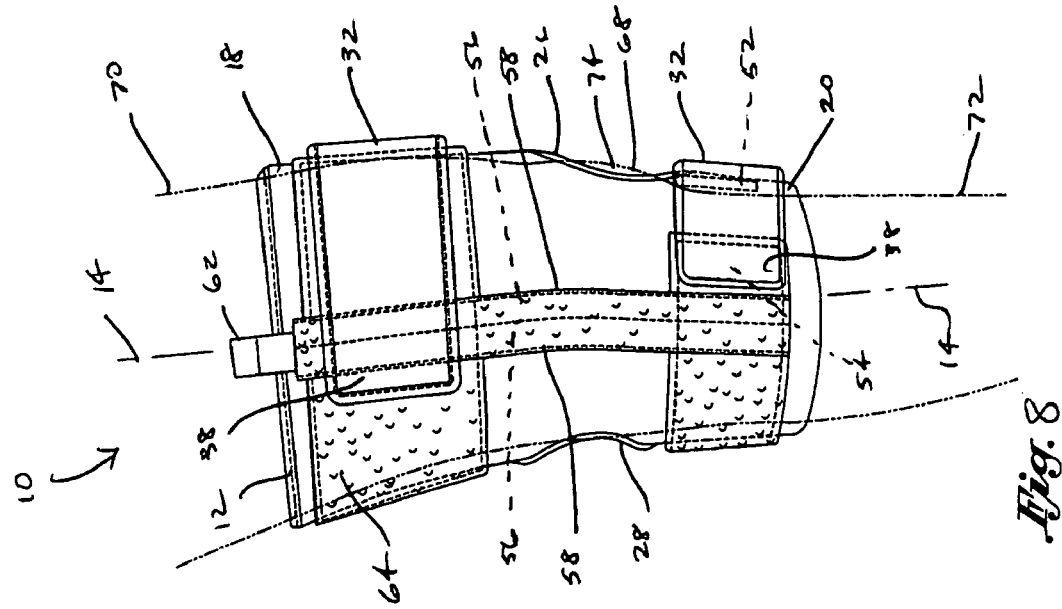
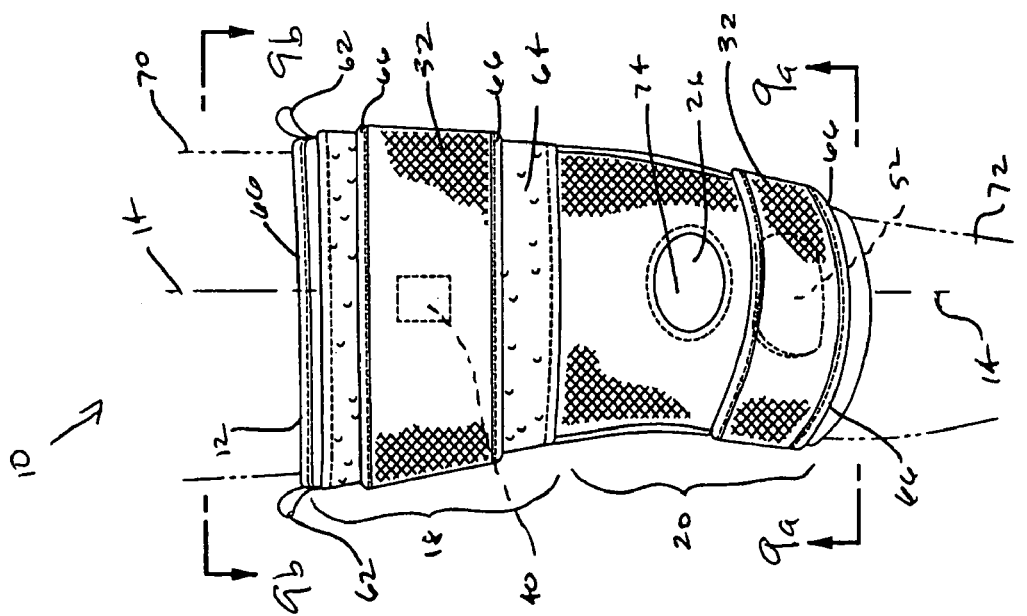

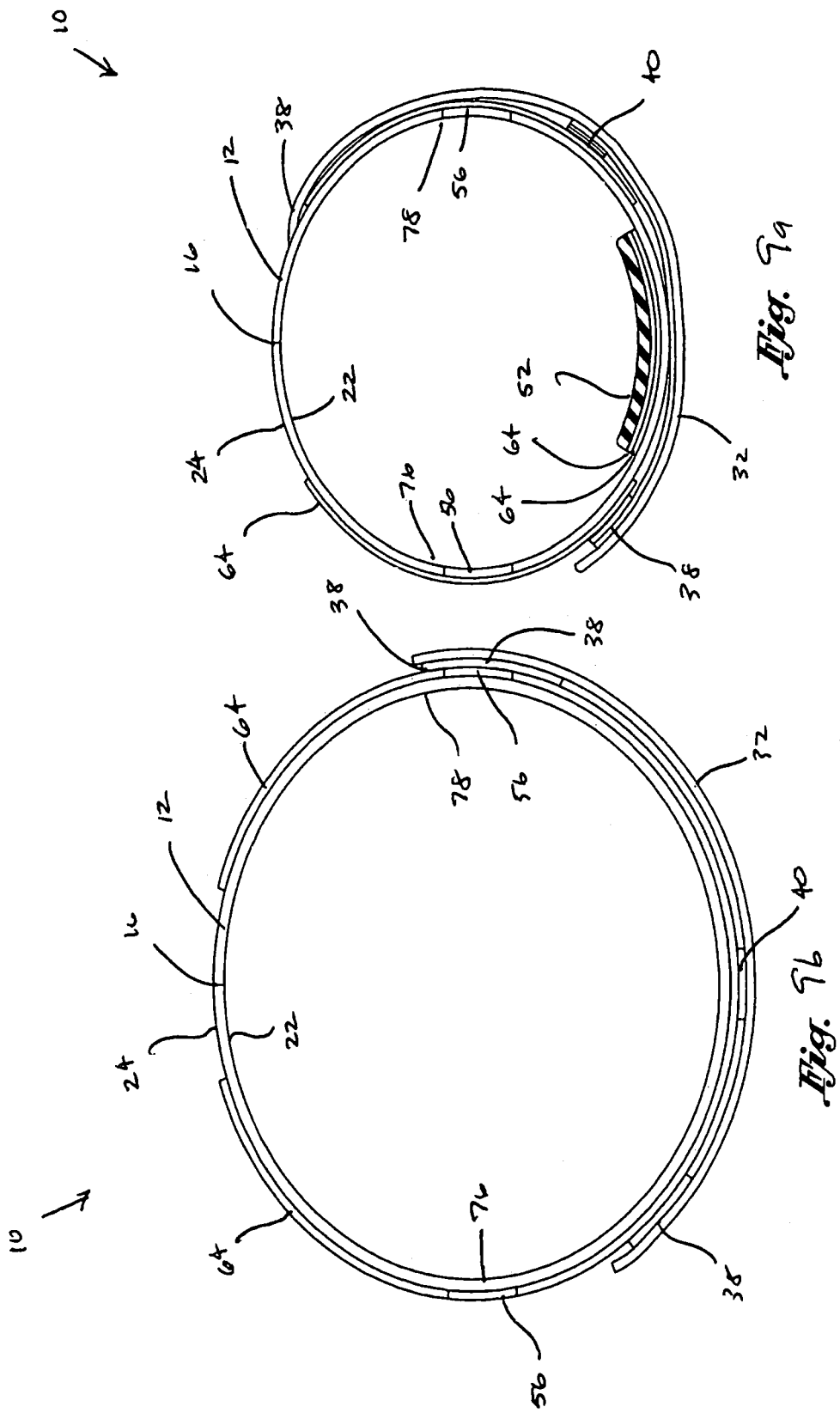

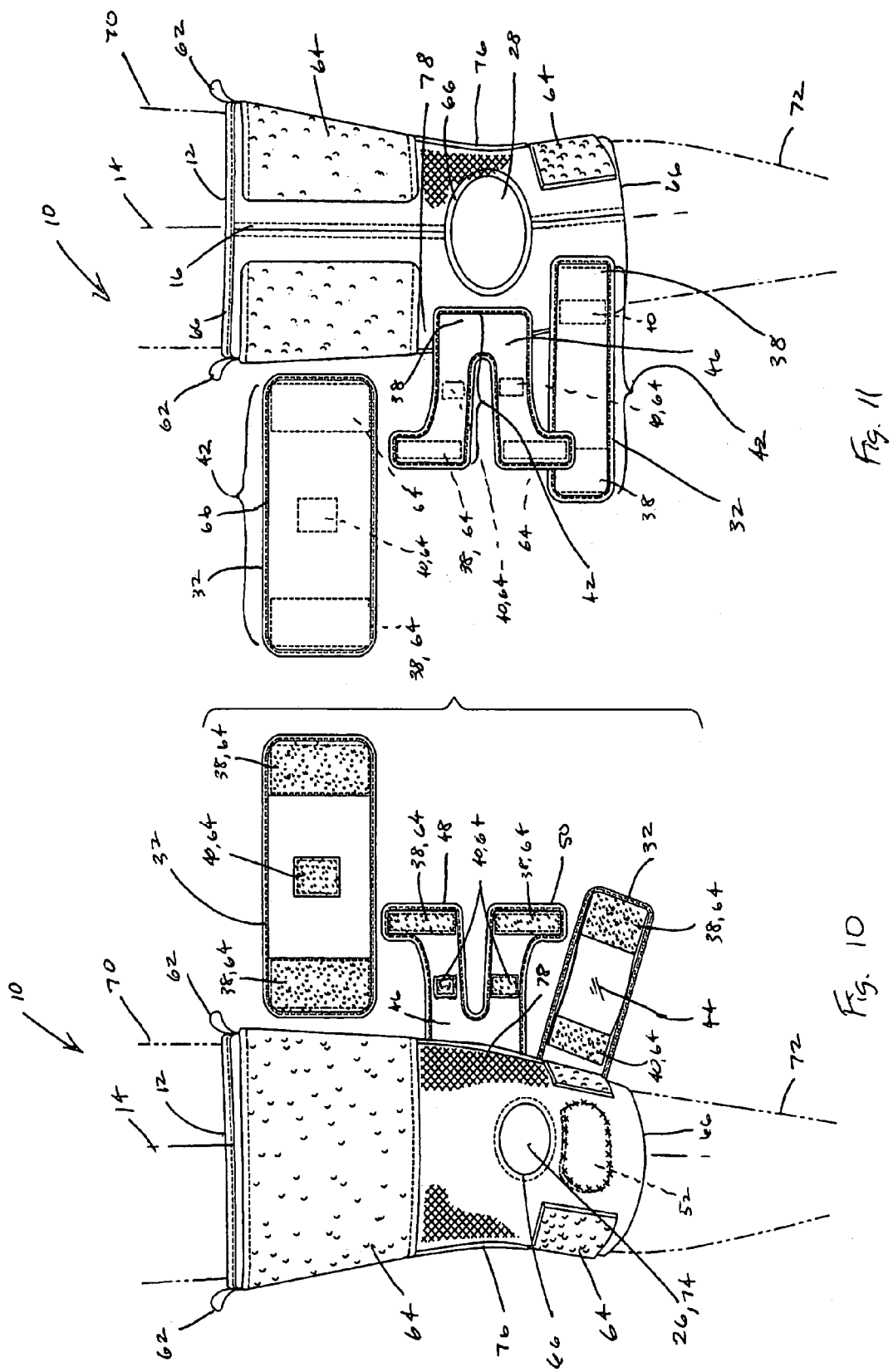

NEUROMUSCULOSKELETAL KNEE SUPPORT DEVICE

CROSS-REFERENCE TO RELATED APPLICATIONS

This application claims the benefit under 35 U.S.C. 119(e) of the filing date of Provisional U.S. Application Ser. No. 60/551,167 and filed on Mar. 8, 2004, which application is expressly incorporated herein by reference

BACKGROUND OF THE INVENTION

This invention relates generally to orthotic devices and, more particularly, to a uniquely configured proprioceptive knee brace specifically adapted to support a patient's knee while providing the benefits of neuromuscular stimulation.

The human knee has an intricate anatomy and a relatively complex set of rotational movements. The primary movements of the knee comprise flexion and extension respectively defined as rearward and forward rotational movement of the tibia (knee bone), relative to the femur (thigh bone). The knee is subject to complex loads and stresses and is the joint that is most often injured during physical endeavors, including athletic or sporting activities. For example, patellar tendinitis ("jumper's knee") is a painful condition that may result from repetitive running and/or jumping as is common when running and playing basketball, volleyball, tennis, etc.

The act of jumping and hitting the ground may overstress the patellar tendon which attaches the patella (kneecap) to the tibia, at the tibia tubercle (upper front portion) of the tibia. Patellar tendinitis is characterized by inflammation of the patellar tendon and surrounding soft tissue in an area just below the patella at the patella/patellar tendon junction. Osgood-Schlatter disease, a condition similar to patellar tendinitis, may occur in young children and adolescents and may be caused by a common phenomenon in children and adolescents wherein the bones grow at a faster rate than that of the muscles and tendons, causing tightness and pulling in the tendons and resulting in pain and inflammation.

Other conditions associated with the patella/patellar tendon junction include chondromalacia patellae, which is a condition characterized by a softening and subsequent breakdown and roughening of articular cartilage lining the patella. Ideally, the articular cartilage is smooth such that it may glide freely along the articular groove of the femur as the knee flexes or bends. Chondromalacia patellae may occur in older age groups as a result of normal wear and tear with aging. This condition may also occur in young children as a result of muscle imbalances around the knee, causing uneven wear on the lateral (outer) facet of the patella.

When chondromalacia patellae occurs in young children, it may be due to an imbalance between vastus lateralis (outer) and vastus medialis (inner) components of the quadriceps muscle, which is the large muscle on the front of the thigh. The quadriceps muscle attaches to the patella via the quadriceps tendon, which is located above the patellar tendon. In some patients, the vastus lateralis may be more powerful than the vastus medialis, resulting in a tendency for the patella to track laterally or outwardly and eventually resulting in softening and breakdown of the patella.

Still other conditions of the knee joint include meniscal (cartilage) tears, wherein shock absorption, joint stabilization, and lubrication qualities otherwise provided by the meniscal cartilage are compromised. Illio-tibial band (ITB) syndrome may occur in long distance runners as a result of running on cambered surfaces or using shoes having little cushioning. The ITB is a relatively thick strip of tendon extending downwardly from the hip joint and passing across the outside of the knee and inserting into the tibia just below the knee joint. ITB syndrome is characterized by pain in the knee joint during flexion and extension as the ITB moves backwards and forwards across the lateral side of the knee joint.

Patello-femoral pain-syndrome (PFPS), or "runner's knee", may be defined as pain resulting from physical changes in the patellofemoral joint (the joint between the femur and the patella), which often worsens with certain activities, such as descending steps or hills. PFPS may be the result of a maltracking of the patella relative to the femur during knee flexion and extension. More specifically, PFPS may be due in part to an imbalance in the quadriceps muscles that attach to the patella. Although balance in the quadriceps muscle assists in the proper tracking of the patella, imbalance in the quadriceps muscle may cause abnormal gliding of the patella leading to eventual inflammation and pain. Similar to the above-described condition of chondromalacia patellae in young children, PFPS may also be caused by an imbalance in muscle strength between the vastus lateralis and the vastus medialis, resulting in a tendency for the patella to track laterally, causing increased stress to the knee joint.

The prior art includes many knee braces that are intended to reduce strain on injured knee components such that the knee may properly heal. Additionally, prior art knee braces may be worn as a preventative measure when the patient engages in strenuous or physically demanding activities. Unfortunately, many knee braces of the prior art suffer from several deficiencies that detract from their overall utility. For example, many of the prior art knee braces are configured to circumferentially wrap around or encircle the patient's knee so as to provide inward compressive force around the circumference of the knee joint. Such knee braces may be designed with the intention of supporting the knee joint against hyperextension, which may stretch or further damage the ligaments and tendons connected thereto. Unfortunately, such circumferential compression about the knee joint causes vascular restriction, which impedes the flow of blood to the injured area and which may extend the healing process.

For the above-described conditions of chondromalacia patellae and PFPS, wherein the vastus lateralis tends to be more powerful than the vastus medialis with resulting patellar tracking dysfunction, some prior art knee braces have been developed with the intention of correcting lateral patella tracking by providing a knee brace configuration that physically pulls or forces the patella in a medial (inward) direction. One such prior art knee brace includes a sleeve having a crescent-shaped side support adaptable to a particular shape of the patient's patella. When tractioned medially across the patella, the knee brace is understood to improve patellafemoral mechanics during knee flexion and extension.

Unfortunately, knee braces of the type described above are typically effective in providing patellar stability and reducing PFPS only when the knee brace is worn. If the knee brace is not worn, further injury to the patella may occur with corresponding pain and discomfort to the patient. Furthermore, as understood, such knee braces are adapted to generally provide treatment in healing injuries and correcting deficiencies in the knee joint using a musculoskeletal stimulation approach with little regard for neurostimulation aspects of healing. In this regard, such knee braces of the prior art, as known and understood by the present inventor, are not believed to provide the best approach to overcoming the wide array of problems associated with the knee joint.

For example, it is believed that knee braces of the prior art are inadequate in correcting patellar tracking dysfunction by merely physically pulling medially on the patella. Moreover, it is believed that knee braces of the prior art are generally ineffective in altering and correcting for muscle imbalances around the knee joint. Finally, it is believed that knee braces of the prior art fail to account for healing qualities provided through neuromuscular stimulation of numerous sensory receptors located on the patient's skin. More specifically, it is noted that one square inch of skin typically contains about 19,000 of such sensory cells, which provide information regarding at least five different senses (pain, heat, cold, touch, and pressure) to the central nervous system.

In this regard, it is believed that providing such neuromuscular stimulation to the skin surrounding the knee joint may stimulate another type of receptor called proprioceptive or stretch receptors, which are located in the muscles and tendons. Proprioceptive response relates to nerves that transmit signals to and from muscles and joints in order to control movement and function of the joints and surrounding areas. Such stretch receptors sense changes in length and tension of muscles and tendons and send information regarding such changes to the central nervous system. Proprioceptive response provides the patient with spatial orientation information regarding location and movement of joints and limbs without the patient actually seeing the limb move.

It is believed that stimulation of the proprioceptive receptors in tissue surrounding the knee joint (i.e., nerves located in the skin, bones, muscle-tendon junctions, and joints) through proprioceptive response creates chemical changes in the body which positively affects the muscles, ligaments, and tendons. More specifically, it is believed that by incorporating proprioceptive response into a knee brace, muscles and tendons surrounding the affected or injured area of the knee joint may be re-educated in proper positioning and relative movement in order to correct for abnormalities and dysfunction in the knee joint such that, over time, adverse knee conditions may be corrected.

As can be seen, there exists a need in the art for a knee brace that can alleviate symptoms of pain and discomfort associated with knee joint degeneration due to injury, wear and tear, or normal aging. Moreover, there exists a need in the art for a knee brace that provides a desired amount of focused compression on tissue surrounding the affected knee joint with minimal vascular restriction on surrounding portions of the knee joint. Additionally, there exists a need in the art for a knee brace wherein a desired amount of medial influence on the patella can be provided in order to compensate and correct for lateral patella tracking dysfunction. Furthermore, there exists a need in the art for a knee brace that combines neuromuscular stimulation with such medial influence and focused compression in order to provide the benefits of proprioceptive response in healing degeneration in the knee joint.

SUMMARY OF THE INVENTION

The present invention specifically addresses and alleviates the above noted deficiencies associated with knee braces of the prior art. More particularly, the present invention is an improved knee brace comprising a stretchable, generally tubular sleeve having an inner sleeve surface and an outer sleeve surface. Each embodiment of the knee brace disclosed herein also has at least one anchor strap mounted on the outer sleeve surface and a viscoelastic pad mounted on the inner sleeve surface. In one embodiment, the knee brace is configured to envelope a portion of the patient's leg generally below the patient's knee with the viscoelastic pad being positioned such that localized pressure may be applied to the patient's infrapatellar tendon. This first embodiment is particularly directed toward patients who may be suffering from injuries related to the patella/infrapatellar junction, in a condition more commonly referred to as "jumper's knee".

The sleeve of the knee brace of a second disclosed embodiment includes upper and lower sleeve portions respectively enveloping a lower portion of a patient's thigh and an upper portion of the patient's calf, as well as the patient's knee. The knee brace of this embodiment includes an anchor strap mounted on the lower sleeve portion and a viscoelastic pad positioned in a manner similar to that in the above described first embodiment. The knee brace of this second embodiment includes an additional anchor strap mounted on the upper sleeve portion and is generally directed toward patients who may be suffering from a condition commonly referred to as "runner's knee".

In yet another embodiment, a knee brace is configured similarly to that above described, with the addition of a patella strap mounted on the lower sleeve portion between the anchor straps of the upper and lower sleeve portions. The patella strap bifurcates into separate segments comprised of an upper patella strap portion and a lower patella strap portion to allow for flexibility in the amount and angular direction with which compressive force may be applied to the patient's patella. The sleeves of each of the above described embodiments each define a sleeve axis extending axially therethrough. Hemming may be applied around upper and lower edges of the anchor straps and the patella strap, as well as to the sleeve in order to minimize fraying and tearing of the elastomeric material and to prevent chafing of the patient's skin against otherwise rough edges of the sleeve.

Importantly, each of the anchor straps of the knee braces of each described embodiment is provided with a double anchor fastening mechanism, comprised of a combination of a pair of end anchor portions and an intermediate anchor portion mounted therebetween. The patella strap described above as part of the third disclosed embodiment is also equipped with such a double anchor fastening mechanism. Such double anchor fastening mechanism provides additional stability of the knee brace against rotational slippage during medial tractioning of the anchor and patella straps. In addition, the double anchor fastening mechanism facilitates the neuromuscular stimulation features provided by the viscoelastic pad when the anchor strap and patella straps are tractioned medially across a patient's knee, thereby providing the benefits of proprioceptive response in facilitating correction of conditions such as patella tracking dysfunction.

A traction pad may be mounted on the inner sleeve surface of the sleeve opposite one of the end anchor portions of each one of the anchor straps, as well as opposite the end anchor portion of the patella strap. The traction pad may provide increased resistance against such rotational slippage, as well as allowing for effective focusing of compressive force by the viscoelastic pad against the patient's skin for increased neuromuscular stimulation. In addition, it should be noted that each one of the knee braces as disclosed in each embodiment may be provided in left-hand and right-hand versions that are distinguishable by fixed securement of the anchor straps on a lateral side of the patient's knee such that the anchor straps and patella strap may be medially tractioned across the patient's knee.

The sleeve of each above disclosed embodiment is preferably fabricated of elastomeric material, such as closed cell foam having four-way stretch capability such that the sleeve may be easily pulled over the knee joint as well as allowing the sleeve to tightly conform to the shape and contours of the knee joint during both static and dynamic modes of knee flexion and extension. In addition, the elastomeric material preferably provides favorable warmth, durability and stability characteristics such as that which may be provided by neoprene. In order to provide neuromuscular stimulation characteristics, the neoprene may include a pattern of relatively small images printed on one side thereof. The elastomeric material may have a thickness within a range of about one millimeter (mm) to about four mm, although elastomeric materials of any thickness may be used.

Each of the above described knee braces has an extendable anchor strap wrappable about the outer sleeve surface, and defining an inner strap surface and an outer strap surface. The anchor strap is preferably fabricated of elastomeric material similar to that which is used to fabricate the sleeve. The anchor strap has end anchor portions and an intermediate anchor portion disposed on the inner strap surface between opposing ones of the end anchor portions. One of the end anchor portions is preferably fixedly secured (e.g. by sewing) to the outer sleeve surface at a position that is disposed adjacent to a lateral side of the patient's knee. The other one of the end anchor portions is generally freely disposed and may comprise a hook and loop panel (such as VELCRO®) such that the end anchor portion may be releasably secured to the outer sleeve surface and pulled medially across the knee joint at a desired degree of tension.

Likewise, the intermediate portion of the anchor strap may include a hook and loop panel with an outer sleeve surface including complementary mating hook and loop panels such that the intermediate anchor portion and the end anchor portion may be releasably secured thereto. The knee brace may further include an elastic band extending along the inner strap surface and being preferably freely disposed thereagainst such that the elastic band may slide against the outer strap surface when the anchor strap is tractioned across the knee joint. The elastic band may be fabricated from any material (e.g woven polyester) having appropriate stretch, recovery and spring characteristics such that tension may be continuously applied about the patient's knee.

As was earlier mentioned, the viscoelastic pad is securable on the inner sleeve surface generally opposite to the elastic band and may be biased toward the upper edge of the sleeve such that localized pressure may be applied to the patient's infrapatellar tendon when the anchor strap is extended over the outer sleeve surface, and the intermediate and end anchor portions are secured thereto. The viscoelastic pad may be releasably secured to the inner sleeve surface such as by means of a hook and loop panel (i.e. VELCRO®) with the inner sleeve surface including a mating hook and loop panel mounted thereon such that the viscoelastic pad may easily be repositioned at a location that provides the compression on the affected area of the patient's knee joint. The viscoelastic pad is preferably fabricated of material that is at least partially comprised of silicone rubber, although any material having resilient characteristics may be utilized.

Regarding the knee brace of the second embodiment described above, the lower sleeve portion is similar to that of the knee brace of the first embodiment. Moreover, the knee brace of the second embodiment includes an upper sleeve portion extending upwardly from the lower sleeve portion and having an anchor strap disposed thereon which is configured similar to that of the lower sleeve portion, with the exception that both of the end anchor portions are releasably securable, such as with VELCRO®. In this manner, the knee brace of the second embodiment may accommodate wide variations in anatomical differences between thighs of different patients. The knee brace of the second embodiment also includes a viscoelastic pad that is preferably positionable on the inner sleeve surface, such that localized pressure may be applied to an area adjacent to the patient's infrapatellar tendon.

In addition, the knee brace of the second embodiment includes a patella hole formed through the sleeve to keep unwanted pressure off of the patella and a popliteal hole positioned generally diametrically opposite of the patella hole to limit bunching of the sleeve in the popliteal region of the knee during knee flexion. The knee brace of the second embodiment may include a pair of elongate stays extending along a length of the sleeve on diametrically opposed sides thereof. Fabricated as a strip of resilient material such as plastic, the stays may provide stability to the knee brace during knee flexion. Pull tabs may be provided along the upper edge of the sleeve such that the patient may pull the sleeve up over the patient's knee by inserting fingers through the pull loops.

The knee brace of the third embodiment is similar to the knee brace of the second embodiment with the exception of the patella strap, which may be fabricated of elastomeric material similar to that which may be used to fabricate the sleeve and the anchor straps. The patella strap is preferably fixedly secured to the outer sleeve surface such as by sewing on the same side as that of the anchor strap of the lower sleeve portion. The traction pad may be secured to the inner sleeve surface by sewing or any other suitable means. The patella strap splits or bifurcates into the upper and lower patella strap portions, each having the intermediate anchor portion disposed between respective ones of the end anchor portions to allow for flexibility regarding the angle at which compression may be applied to the patient's patella. Each one of the intermediate anchor portions, and at least one of the end anchor portions of the upper and lower patella strap portions includes a hook and loop panel (i.e. VELCRO®) mounted thereon in the same manner as that described above for the anchor straps.

The invention, together with additional features and advantages thereof, may be best understood by reference to the following description taken in conjunction with the accompanying illustrative drawings. In these accompanying drawings, like reference numerals designate like parts throughout the figures.

BRIEF DESCRIPTION OF THE DRAWINGS

FIG. 1 is a perspective view of a knee brace in a first embodiment enveloping a patient's leg at a location generally below the patient's knee and having a viscoelastic pad secured to an inner sleeve surface;

FIG. 2 is a front view of the knee brace of the first embodiment, illustrating an anchor strap extending across an anterior portion of the patient's knee;

FIG. 3 is a rear view of the knee brace of the first embodiment illustrating the securement of an end anchor portion of the anchor strap on an outer sleeve surface;

FIG. 4a is a cross-sectional view of the knee brace of the first embodiment taken along section 4a-4a of FIG. 3 and illustrating the relative positioning of the anchor strap and the viscoelastic pad when the anchor strap is extended across the patient's knee;

FIG. 4b is a partially exploded cross-sectional view of the knee brace of the first embodiment taken along section 4b-4b of FIG. 3 and illustrating hook and loop panels that may be used to secure the viscoelastic pad and the anchor strap to the sleeve;

FIG. 5 is a partially exploded front view of the knee brace in a second embodiment having upper and lower sleeve portions configured to envelope the patient's knee as well as a lower portion of the patient's thigh and an upper portion of the patient's calf;

FIG. 6 is a partially exploded rear view of the knee brace of the second embodiment illustrating anchor straps configured to be extended across the upper and lower sleeve portions;

FIG. 7 is a front view of the knee brace of the second embodiment illustrating the anchor straps extended across and affixed to the sleeve;

FIG. 8 is a side view of the knee brace of the second embodiment illustrating a stay disposed along sides of the sleeve;

FIG. 9a is a cross-sectional view of the knee brace of the second embodiment taken along section 9a-9a of FIG. 8 and illustrating the relative positioning of the anchor strap on the upper sleeve portion;

FIG. 9b is a cross-sectional view of the knee brace of the second embodiment taken along section 9b-9b of FIG. 8 and illustrating the relative positioning of the viscoelastic pad and the anchor strap on the lower sleeve portion;

FIG. 10 is a partially exploded front view of the knee brace in a third embodiment configured similarly to the second embodiment and having a patella strap interposed between the anchor straps of the upper and lower sleeve portions; and FIG. 11 is a partially exploded rear view of the knee brace of the third embodiment illustrating the fixed securement of the patella strap and the anchor strap of the lower sleeve portion.

DESCRIPTION OF THE PREFERRED EMBODIMENT

Referring now to the drawings, wherein the showings are for the purpose of illustrating the principles of the present invention and not for the purpose of limiting same, there is shown in FIGS. 1-3, 4a, and 4b a knee brace 10 in a first embodiment, wherein the knee brace 10 comprises a stretchable generally tubular sleeve 12 having an inner sleeve surface 22 and an outer sleeve surface 24. The knee brace 10 also has an anchor strap 32 mounted on the outer sleeve surface 24 and a viscoelastic pad 52 mounted on the inner sleeve surface 22. The knee brace 10 of the first embodiment is configured to envelop a portion of the patient's leg at a location generally below the patient's knee. The viscoelastic pad 52 is preferably positioned such that localized pressure may be applied to the patient's infrapatellar tendon, as is shown in FIG. 1. In this regard, the knee brace 10 of the first embodiment is intended for use by patients who may be suffering from injuries related to the junction of the patell/infrapatellar tendon. Such injuries may be characteristic of a condition more commonly referred to as "jumper's knee" as will be described in greater detail below.

Shown in FIGS. 5-8, 9a, and 9b is a knee brace 10 in a second embodiment, wherein the sleeve 12 has an upper sleeve portion 18 and a lower sleeve portion 20, and is configured to extend respectively upwardly and downwardly from the knee 68 itself, as well as wrap around a lower portion of the patient's thigh 70 and an upper portion of the patient's calf 72. The knee brace 10 of the second embodiment includes an anchor strap 32, as in the first embodiment, mounted on the lower sleeve portion 20, with the viscoelastic pad 52 being positioned such that localized pressure may be applied thereto, as is shown in FIG. 9a. The knee brace 10 of the second embodiment includes an additional one of the anchor straps 32 which is mounted on the upper sleeve portion 18 to facilitate healing of a condition commonly known as "runner's knee", as will be described in greater detail hereinbelow.

The anchor strap 32 of the lower sleeve portion 20 is configured similarly to that of the anchor strap 32 of the first embodiment.

Illustrated in FIGS. 10-11 is a modified knee brace 10 according to yet a third embodiment of the present invention, wherein the sleeve 12 is configured similar to that shown and described in connection with the second embodiment of FIGS. 5-8. However, the knee brace 10 of the third embodiment additionally includes a patella strap 46 mounted on the lower sleeve portion 20 and disposed between the anchor straps 32 of the upper and lower sleeve portions 18, 20. The patella strap 46 may be secured to the outer sleeve surface 24 and may bifurcate into separate segments, including an upper patella strap portion 48 and a lower patella strap portion 50 to allow for flexibility in the amount and direction with which compressive force may be applied to the patient's patella 74. For the knee brace 10 of the third embodiment, the anchor strap 32 of the lower sleeve portion 20 is configured similar to that of the anchor strap 32 of the first and second embodiments. In addition, the sleeves 12, as used and described in the knee braces 10 of the second and third embodiments described herein, each define a sleeve axis 14 extending axially therethrough in a direction similar to the sleeve axis 14 of the first embodiment. Moreover, each one of the sleeves 12 of the knee braces 10 of the second and third embodiments include an inner sleeve surface 22 and an outer sleeve surface 24. Hemming 66 may be applied around upper and lower edges of the sleeve 12 of each of the embodiments to minimize fraying and tearing of the elastomeric material, as is shown in FIGS. 1, 5, and 10. In addition, the hemming 66 may prevent chafing of the patient's skin against otherwise rough edges of the sleeve 12.

Importantly, each of the anchor straps 32 of the knee braces 10 of each of the described embodiments, as well as the patella strap 46 of the third embodiment, is provided with a double anchor fastening mechanism 42. In this regard, the double anchor fastening mechanism 42 is comprised of a combination of end anchor portions 38 and an intermediate anchor portion 40 mounted therebetween, such that the anchor straps 32 and patella strap 46 may be secured to the outer sleeve surface 24. As will be described in greater detail below, the double anchor fastening mechanism 42 provides additional stability of the knee brace 10 against rotational slippage during medial tractioning of the anchor straps 32 and patella strap 46. In addition, the double anchor fastening mechanism 42 facilitates the neuromuscular stimulation features provided by the viscoelastic pad 52 when the anchor strap 32 and patella strap 46 are tractioned medially across the patient's knee 68.

In addition, a traction pad 54 may be mounted on the inner sleeve surface 22 to provide for increased resistance against such rotational slippage and further provide for effective focusing of compressive force by the viscoelastic pad 52 against the patient's skin, resulting in improved neuromuscular stimulation thereto. Furthermore, it should be noted that each one of the knee braces 10 of the first, second, and third embodiments may be provided in left-hand and right-hand versions. In this regard, the anchor straps 32 and patella strap 46 are preferably, but optionally, secured to a lateral side 78 of the knee brace 10. In this manner, the anchor strap 32 and patella strap 46 may be medially tractioned across the patient's knee 68 in a manner as will be described in greater detail hereinbelow.

Referring now once again to the first embodiment shown in FIGS. 1-3, 4a, and 4b, the sleeve 12 is preferably formed as a generally flexible tubular structure constructed of elastomeric material such as closed cell foam. In this regard, the elastomeric material preferably has favorable four-way stretch capability, as well as favorable warmth, durability, and stability characteristics. In addition, the elastomeric material preferably has favorable strength and flexibility characteristics, such that the sleeve 12 may be easily pulled over the knee. However, the elastomeric material is also preferably configured such that the sleeve 12 tightly conforms to the shape and contours of the knee 68 in the area just below the patella 74 in static modes as well as in dynamic modes of knee flexion and extension.

The elastomeric material is preferably at least partially comprised of neoprene. In order to provide neuromuscular stimulation characteristics, the neoprene may include a pattern of relatively small images printed on one side thereof. Neoprene having such a pattern is commercially available under the trademark NEUORPRENE. By fabricating the knee brace 10 such that the pattern is disposed on the inner sleeve surface 22, the knee brace 10 may provide the neuromuscular stimulation characteristics to the patient's knee. The elastomeric material as used for the knee brace 10 may have a thickness in a range of about one mm to about four mm, although elastomeric material of any thickness may be used. The sleeve 12 may be fabricated of a flat sheet or generally planar panel of the elastomeric material, joined at a sleeve seam 16 to form a generally cylindrical configuration.

For the knee brace 10 of the first embodiment, the sleeve 12 may have a width of about four inches on one side of the sleeve 12 and a width of about three and one-half inches on an opposing one of the sides of the sleeve 12. Taping may be applied along a length of the sleeve seam 16 on the inner sleeve surface 22 to provide a smooth surface to bear against the patient's skin. Although shown as being joined by sewing and/or gluing at the sleeve seam 16, it is contemplated that the sleeve 12 may be formed in a tubular shape through the use of mating hook and loop panels 64 or mechanical fasteners such as snaps, buttons, or the like. However, sewing the sleeve seam 16 and taping the inner sleeve surface 22 thereat is considered to be advantageous.

As shown in FIGS. 1-3, 4a and 4b, the knee brace 10 includes the extendable anchor strap 32, wrappable about the outer sleeve surface 24 and defining an inner strap surface 34 and an outer strap surface 36. The anchor strap 32 is preferably fabricated of elastomeric material and has a generally elongate shape. Hemming 66 may be applied around a perimeter of the anchor strap 32 to prevent fraying and tearing of the elastomeric material. Regarding the type of elastomeric material from which the anchor strap 32 may be fabricated, it is contemplated that material that is at least partially comprised of neoprene may be utilized, although any closed cell foam having the desirable flexibility and strength characteristics may be used. The anchor strap 32 has opposing end anchor portions 38 and an intermediate anchor portion 40 disposed on the inner strap surface 34, between opposing ones of the end anchor portions 38. One of the end anchor portions 38 is preferably fixedly secured to the outer sleeve surface 24 at an angular position that is lateral to the sleeve seam 16. The anchor strap 32 of the first embodiment preferably has a width of about two and one-half inches, although the anchor strap 32 may be provided in any width.

The traction pad 54 may be secured to the inner sleeve surface 22 generally opposite to the location of the end anchor portion 38. The traction pad 54 may be generally triangularly shaped, although any shape may be suitable, within the scope of the invention. The traction pad 54 may be sewed to the inner sleeve surface 22, although any suitable attachment means may be used. The fixed securement of the end anchor portion 38 may be by means of sewing, although alternative means such as gluing may be utilized to fixedly secure the end anchor portion 38 to the outer sleeve surface 24. The other one of the end anchor portions 38 is generally freely disposed, such that the end anchor portion 38 may be pulled medially across the knee 68 at a desired degree of tension and then preferably releasably secured to the outer sleeve surface 24. In addition, such releasable securement allows the tension in the anchor strap 32 to be selectively adjusted, as shown in FIGS. 4a and 4b. The intermediate anchor portion 40 of the anchor strap 32 is placed generally between the end anchor portions 38, but may be biased toward the one of the end anchor portions 38 that is fixedly secured to the outer sleeve surface 24. As is shown in FIG. 4a, the intermediate anchor portion 40 is spaced apart from the end anchor portion 38.

Both the intermediate anchor portion 40 and end anchor portion 38 may include a releasable securing panel, such as a hook and loop panel 64, that is mounted on the inner strap surface 34. The outer sleeve surface 24 may include complementary mating hook and loop panels 64 mounted thereon such that the intermediate anchor portion 40 and the end anchor portion 38 may be releasably secured thereto to allow for selective adjustment of tension in the anchor strap 32. The hook and loop panel 64 of the intermediate anchor portion 40 generally spans a width of the anchor strap 32. The hook and loop panel 64 of the anchor strap 32 may also generally span the width of the anchor strap 32. It should be noted that, although the hook and loop panels 64 are shown with a generally rectangular shape, such hook and loop panels 64 may be provided in any size and shape sufficient to provide the double anchor fastening mechanism 42. It should be noted that, although hook and loop panels are the preferred securing system for use in the invention, any other known releasable securing devices may be utilized, such as snaps, buttons, mechanical fastening systems, and the like.

Referring still to FIGS. 1-3, 4a and 4b, the knee brace 10 may further include an elastic band 44 extending along the inner strap surface 34 between the intermediate anchor portion 40 and one of the end anchor portions 38. The elastic band 44 is preferably freely disposed against the inner strap surface 34 and is only held thereagainst due to connection at the intermediate end anchor portions 40, 38. In this regard, the elastic band 44 may slide against the outer strap surface 36 when the anchor strap 32 is tractioned across the knee 68. The elastic band 44 may be fabricated from a variety of alternative materials, although preferably the elastic band 44 is fabricated from a material having appropriate stretch, recovery and spring characteristics such that tension may be continuously applied about the patient's leg in order to stabilize the position of the viscoelastic pad 52 and prevent movement during daily activities of the patient. In this regard, the elastic band 44 may be at least partially comprised of woven polyester. Alternatively, the elastic band 44 may be fabricated of material comprised of natural fibers such as cotton or of synthetic fibers including polyester, nylon and polypropylene or any other suitable material or in any combination thereof.

For the knee brace 10 of the first embodiment, at least one viscoelastic pad 52 is preferably included therewith and is securable on the inner sleeve surface 22 generally opposite to the elastic band 44 when the anchor strap 32 is tractioned across the knee 68. The viscoelastic pad 52 may be generally disposed toward the upper edge of the sleeve 12 and on a side of the sleeve 12 that is opposite that sleeve seam 16. In this regard, the viscoelastic band 44 is preferably positioned such that localized pressure may be applied to the patient's infrapatellar tendon when the anchor strap 32 is extended over the outer sleeve surface 24 and the intermediate and end anchor portions 40, 38 are secured thereto. The viscoelastic pad 52 may be releasably secured to the inner sleeve surface 22 such as by means of a hook and loop panel 64 mounted thereon, or other suitable releasable securing system. Likewise, the inner sleeve surface 22 may include a mating hook and loop panel 64 mounted thereon such that the viscoelastic pad 52 may be releasably secured thereto as well as be easily repositioned at a location that provides compression on the affected area of the patient's knee 68. The viscoelastic pad 52 is preferably fabricated of material that is at least partially comprised of silicone rubber, although any material having resilient characteristics may be utilized to fabricate the viscoelastic pad 52.

Referring now to FIGS. 5-8, 9a and 9b, shown therein is the knee brace 10 of the second embodiment. The lower sleeve portion 20 is similar to the knee brace 10 of the first embodiment. Moreover, the anchor strap 32 of the lower sleeve portion 20 is configured similarly to that of the first embodiment in its construction as well as in its preferably fixed securement at one of the end anchor portions 38. The anchor strap 32 preferably has a width of about two and one-half inches, although the anchor strap 32 of the lower sleeve portion 20 may be provided in any width. The knee brace 10 of the second embodiment includes the upper sleeve portion 18 extending upwardly from the lower sleeve portion 20. The upper sleeve portion 18 is configured to envelop a portion of the patient's knee 68 and thigh 70. In this regard, the upper and lower sleeve portions 18, 20 extend respectively upwardly and downwardly to encircle portions of the patient's lower thigh 70 and upper calf 72.

Each of the upper and lower sleeve portions 18, 20 is circumferentially wrappable about the outer sleeve surface 24 in a manner similar to that of the knee brace 10 of the first embodiment. The knee brace 10 of the second embodiment also includes an anchor strap 32 disposed on the upper sleeve portion 18 and having end anchor portions 38 and the intermediate anchor portion 40, as shown in FIGS. 5-8. The anchor strap 32 on the upper sleeve portion 18 may have a width of about four inches, although the anchor strap 32 may be provided in any width. In this manner, the knee brace 10 of the second embodiment may accommodate variations in anatomical differences of thighs. In addition, tension in the anchor strap 32 of the upper sleeve portion 18 may be selectively adjusted by providing the end anchor portions 38 as being releasably securable. The traction pads 54 may be mounted on the inner sleeve surface 22 opposite to the end anchor portion 38 mounting areas on a lateral side 78 of the sleeve 12. In this manner, the traction pads 54 may engage the patient's skin for medially tractioning thereof across the knee 68 without undue slippage of the sleeve 12.

The knee brace 10 of the second embodiment includes the anchor strap 32 of the lower sleeve portion 20, having the elastic band 44 extending along the inner strap surface 34 between the intermediate anchor portion 40 and one of the end anchor portions 38. The knee brace 10 of the second embodiment also includes the viscoelastic pad 42 that is preferably releasably securable on the inner sleeve surface 22 of the lower sleeve portion 20 and positioned in a manner similar to that of the viscoelastic pad 52 of the first embodiment described above. More particularly, the viscoelastic pad 52 is positionable on the inner sleeve surface 22 generally opposite to the elastic band 44, such that localized pressure may be applied to an area adjacent to the patient's infrapatellar tendon when the anchor strap 32 is extended thereover and the intermediate and end anchor portions 40, 38 are secured to the outer sleeve surface 24.

Importantly, in the knee brace 10 of the second embodiment, the lower sleeve portion 20 includes a patella hole 26 in order to keep unwanted pressure off of the patella 74. The lower sleeve portion 20 may also include a popliteal hole 28 formed therethrough and being positioned generally diametrically opposite to the patella hole 26. The popliteal hole 28 is preferably configured to be aligned with a popliteal region of the knee 68 on a posterior side thereof. Preferably, the patella hole 26 is anatomically sized in a generally circular shape to accommodate the patient's patella 74, although other shapes may be utilized. The popliteal hole 28 may optionally be included in the sleeve 12 and may include a lawyer of popliteal webbing 30 of elastomeric material such as nylon webbing or material known under the trademark LYCRA. The popliteal hole 28 is configured to limit bunching of the sleeve 12 in the popliteal region of the knee 68 during knee flexion. As is shown in FIG. 7, the viscoelastic pad 52 is generally positionable below the patella hole 26 such that focused compression may be applied to the area just below the patella 74.

Referring still to FIGS. 5-8, 9a and 9b, the knee brace 10 of the second embodiment may optionally include a pair of elongate stays 56 extending along a length of the sleeve 12 in general alignment with the sleeve axis 14. The stays 56 may be fabricated as a strip of resilient or semi-resilient material such as plastic, although any material may be used that can provide stability to the knee brace 10. Although FIG. 8 shows a pair of stays disposed in side-by-side arrangement on diametrically opposed sides of the sleeve 12, any number of the stays 56 may be provided. Preferably, the stays 56 are positioned such that they are generally disposed on lateral and medial sides 78, 76 of the knee 68. Each one of the stays 56 is generally centered within an area between the patella hole 26 and the popliteal hole 28 and may be encapsulated within a stay pocket 60 formed by a stay cover 58. Although the stay covers 58 may be formed of elastomeric material such as the neoprene material described above, in order to provide additional surface area upon which the anchor straps 32 may be mounted, the stay covers 58 may be comprised of hook and loop panel 64 material. Pull tabs 62 may optionally be provided along the upper edge of the upper sleeve portion 18 such that the patient may pull the sleeve 12 up the patient's leg and over the knee 68. As shown in FIG. 8, the pull tabs 62 may be generally aligned with the stays 56. The pull tabs 62 are preferably fabricated of inelastic material such as cotton or polyester webbing sewn into the sleeve 12 and may be configured as loops through which the patent's fingers may be inserted.

Referring now to FIGS. 10-11, shown is the knee brace 10 of the third embodiment which is identical to the knee brace 10 of the second embodiment with the exception of an extendable patella strap 46. The patella strap 46 is mounted on the outer sleeve portion 12 between the anchor straps 32 of the upper and lower sleeve portions 18, 20. The patella strap 46 may be fabricated of elastomeric material similar to that which may be used to fabricate the anchor straps 32. The patella strap 46 is preferably fixedly secured such as by sewing to the outer sleeve surface 24 at an end anchor portion 38 of the patella strap 46. An additional one of the traction pads 54 may be mounted opposite to the end anchor portion 38 of the patella strap 46. Because the patella strap 46 may be medially tractioned from the lateral side 78 of the knee 68 to a medial side 76, the patella strap 46 is preferably fixedly secured to the sleeve 12 on the same side as that of the anchor strap 32 of the lower sleeve portion 20. The traction pad 54 may be secured to the inner sleeve surface 22 by sewing or any other suitable means. As can be seen in FIGS. 10-11, the patella strap 46 splits or bifurcates into an upper patella strap portion 48 and a lower patella strap portion 50. Each one of the upper and lower patella strap portions 48, 50 has an end anchor portion 38 that is freely disposed and which may flare into an enlarged area to provide increased surface are for securement to the outer sleeve surface 24.

Each one of the upper and lower patella strap portions 48, 50 further includes an intermediate anchor portion 40 disposed between respective ones of the end anchor portions 38. In the same manner as that described above for the end anchor portions 38 of the anchor straps 32, the end anchor portions 38 of the enlarged areas are configured to be releasably securable to the outer sleeve surface 24. Likewise, the intermediate anchor portions are also configured to be releasably securable to the outer sleeve surface 24. In this manner, localized pressure may be applied to the patient's patella 74 when the upper and lower patella strap portions 48, 50 are extended thereover. Moreover, the bifurcated nature of the patella strap 46 allows for flexibility regarding the angle of application and degree of compression that may be applied to the patient's patella 74. Each one of the intermediate anchor portions and at least one of the end anchor portions 38 of the upper and lower patella strap portions 48, 50 includes a hook and loop panel 64 mounted thereon in the same manner as that described above for the anchor straps 32. The outer sleeve surface 24 includes complementary hook and loop panels 64 such that the intermediate and end anchor portions 40, 38 may be releasably secured thereto.

The operation of the knee braces 10 of the first, second, and third embodiments will now be described with initial reference to FIGS. 1-3, 4a and 4b. The knee brace 10 of the first embodiment is pulled over the patient's calf 72 up to a position just below the patient's patella 74 with the sleeve seam 16 being positioned adjacent to the popliteal region of the knee 68. If desired, the viscoelastic pad 52 may be positioned on the inner sleeve surface 22 prior to pulling the knee brace 10 over the patient's calf 72. Preferably, there are left hand and right hand versions of the knee brace, such that the anchor strap 32 is always fixedly positioned on the lateral side 78 of the knee 68. The traction pad 54, also secured to the inner sleeve surface 22 opposite to the end anchor portion 38, is preferably positioned about one inch medial to a posterior head of the patient's fibula. Once the knee brace 10 is positioned as described above, the anchor strap 32 may be tractioned medially across the lateral side 78 of the knee 68 until the intermediate anchor portion 40 is engaged to the outer sleeve surface 24. Following securement of the intermediate anchor portion 40 of the anchor strap, the anchor strap 32 is further medially tractioned across anterior surfaces of the knee 68 until a desired amount of focused compression is applied by the viscoelastic pad 52 against the patient's skin. The end anchor portion 38 is then secured to the medial side 76 of the knee 68 to provide the double anchor fastening mechanism 42. The end anchor portion 38 and the intermediate anchor portion 40 of the anchor strap 32 may be releasably secured using the hook and loop panels 64, more commonly referred to as VELCRO®.

The operation of the second and third embodiments of the knee brace 10 will now be described with reference to FIGS. 5-11. Following securement of the viscoelastic pad 52 on the inner sleeve surface 22, the knee brace 10 may be puled over the patient's knee 68 by the pull tabs 62 such that the upper sleeve portion 18 encircles the patient's lower thigh 70 and the viscoelastic pad 52 is positioned just below the patella 74 in the same manner as that described above in connection with the first embodiment. The anchor strap 32 of the lower sleeve portion 20 is tractioned medially across the knee 68 in the same manner as in the first embodiment. The anchor strap 32 of the upper sleeve portion 18 is then applied on the lateral side 78 of the thigh 70 using the hook and loop panel 64. The anchor strap 32 is tractioned across the anterior portion of the patient's lower thigh 70 until the intermediate anchor portion 40 is secured to the outer sleeve surface 24. The anchor strap 32 is then again medically tractioned across the medial side 76 of the patient's thigh 70 after which the remaining one of the end anchor portions 38 is secured to the outer sleeve surface 24.

The operation of the third embodiment of the knee brace 10 is identical to that described above for the second embodiment, with the exception of the application of the patella strap 46, which may be performed after application of the anchor straps 32 of the upper and lower sleeve portions 18, 20. As was previously described, one of the end anchor portions 38 of the patella strap 46 is preferably fixedly secured to the sleeve 12 on a same side as that of the anchor strap 32 of the lower sleeve portion 20. The upper patella strap portion 48 and lower patella strap portion 50 are then tractioned medially across the patient's patella 74, with the intermediate anchor portions 40 thereof being secured to the outer sleeve surface 25 on the anterior of the patient's knee 68. Depending upon the angle at which the upper and lower patella strap portions 48, 50 are disposed relative to one another, one of the intermediate anchor portions 40 may be applied to one of the upper and lower patella strap portions 48, 50. The remaining one of the end anchor portions 38 of the upper and lower patella strap portions 48, 50 are then secured to the outer sleeve surface 24.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A knee support for proprioceptively treating a wearer, comprising:
    a sleeve sized and configured to envelop a portion of a leg of the wearer, the sleeve defining an inner sleeve surface and an outer sleeve surface, the inner sleeve surface being configured to contact a portion of the leg of the wearer;
    an extendable anchor strap wrappable at least partially about the outer sleeve surface, defining an inner strap surface and including opposing end anchor portions, the end anchor portions being securable to the outer sleeve surface such that tension in the anchor strap may be selectively adjusted; and
    at least one viscoelastic pad positioned on the inner sleeve surface generally opposite to at least a portion of the anchor strap when the anchor strap is extended over at least a portion of the outer sleeve surface and the end anchor portions are secured thereto.

2. The knee support as recited in claim 1, wherein:
    the anchor strap includes an intermediate anchor portion disposed on the inner strap surface between the opposing end anchor portions, wherein each of the intermediate anchor portion and at least one of the end anchor portions includes a securing device mounted thereon;
    the outer sleeve surface including a complementary securing device so that the intermediate and end portions may be releasably secured thereto, wherein the portion of the inner strap surface between the intermediate anchor portion and the end anchor portion with the securing device cannot be secured to the outer sleeve surface.

3. The knee support as recited in claim 2, wherein the securing device comprises a hook and loop panel, and the said complementary securing device comprises a mating hook and loop panel.

4. The knee support as recited in claim 2 wherein one of the end anchor portions is permanently anchored to the outer sleeve surface and the opposite end anchor portion and the intermediate anchor portion are releasably secured to the outer sleeve surface.

5. The knee support as recited in claim 1, wherein the at least one viscoelastic pad is shaped and positioned to apply localized pressure to the top of the wearer's patella when the sleeve is worn by the wearer.

6. The knee support as recited in claim 1, wherein:
the sleeve and the anchor strap are each fabricated of elastomeric material; and
the sleeve is sized such that inner sleeve surface is generally tightly disposed against the patient's skin when the knee support is worn.

7. The knee support as recited in claim 6, wherein:
the elastomeric material is at least partially comprised of neoprene; and
the viscoelastic pad is fabricated of material that is at least partially comprised of silicone rubber.

8. The knee support as recited in claim 1 wherein the entire viscoelastic pad is positioned generally under the anchor strap when the anchor strap is extended over the outer sleeve surface and the end anchor portions are secured thereto.

9. The knee support as recited in claim 1 wherein when the sleeve is worn by a wearer and the anchor strap is extended over the outer sleeve surface and the end anchor portions are secured thereto, the anchor strap pulls the sleeve and the viscoeleastic pad and the viscoelastic pad pulls the wearer's skin.

10. The knee support as recited in claim 1, wherein the at least one viscoelastic pad is shaped and positioned for applying compressive pressure on the wearer's infrapatellar tendon.

11. The knee support as recited in claim 1, wherein an entire inner surface of the at least one viscoelastic pad is shaped and positioned to contact the wearer's skin.

12. A leg support for proprioceptively treating a wearer, comprising:
a sleeve sized and configured for disposition about a portion of the wearer's leg; and
at least one viscoelastic pad disposed on an inner sleeve surface of the sleeve, wherein the viscoelastic pad applies localized pressure to a desired portion of the skin of the wearer's leg, and wherein the pressure applied by the viscoelastic pad to the desired portion of the skin of the wearer's leg stimulates the proprioceptive receptors in that portion of the wearer's skin
upper and lower sleeve portions extending respectively upwardly and downwardly from the sleeve to envelop portions of the wearer's leg, the sleeve defining a sleeve axis extending axially therethrough and having inner and outer sleeve surfaces; and
a pair of extendable anchor straps disposed on respective ones of the upper and lower sleeve portions and wrappable at least partially about the outer sleeve surface, each one of the anchor straps defining an inner strap surface and having opposing end anchor portions and an intermediate anchor portion disposed therebetween, the end and intermediate anchor portions being securable to the outer sleeve surface such that tension in the anchor straps may be selectively adjusted,
wherein the viscoelectric pad is disposed on the inner sleeve surface of the lower sleeve portion and is positionable generally opposite to at least a portion of the anchor strap, wherein the anchor strap applies pressure to the viscoelastic pad when the anchor strap is extended thereover and the intermediate and end anchor portions are secured to the outer sleeve surface, wherein when the sleeve is worn by a wearer an inner surface of the viscoelastic pad contacts the wearer's skin, and wherein the pressure applied by the anchor strap to the viscoelastic pad stimulates the proprioceptive receptors in the wearer's skin.

13. The leg support as recited in claim 12, wherein:
each of the intermediate anchor portion and at least one of the end anchor portions of each one of the anchor straps includes a securing panel mounted thereon; and
the outer sleeve surface includes complementary mating securing panels mounted thereon such that the intermediate and end anchor portions may be releasably secured thereto.

14. The leg support as recited in claim 13, wherein the securing panel and the complementary mating securing panels comprise hook and loop panels.

15. The leg support as recited in claim 12, wherein: the viscoelastic pad comprises a securing system mounted thereon; and the inner sleeve surface includes a mating system mounted thereon such that the viscoelastic pad may be releasably secured thereto.

16. The leg support as recited in claim 15, wherein the securing system and the mating securing system each comprise a hook and loop panel.

17. The leg support as recited in claim 12, wherein the at least one viscoelastic pad is shaped and positioned for applying compressive pressure on the wearer's infrapatellar tendon.

18. The leg support as recited in claim 12, wherein the pair of extendable anchor straps comprise two distinct extendable anchor straps.

19. A leg support for proprioceptively treating a wearer, comprising:
a sleeve sized and configured for disposition about a portion of the wearer's leg; and
at least one viscoelastic pad disposed on an inner sleeve surface of the sleeve, wherein the viscoelastic pad applies localized pressure to a desired portion of the skin of the wearer's leg, and wherein the pressure applied by the viscoelastic pad to the desired portion of the skin of the wearer's leg stimulates the proprioceptive receptors in that portion of the wearer's skin,
wherein the viscoelastic pad is shaped and positioned to apply localized pressure to the top of the wearer's patella when the sleeve is worn by the wearer.

* * * * *